(12) United States Patent
Jones et al.

(10) Patent No.: US 8,475,396 B2
(45) Date of Patent: Jul. 2, 2013

(54) METHOD AND SYSTEM OF AN ACOUSTIC SCENE ANALYZER FOR BODY SOUNDS

(75) Inventors: Kevin Jones, Gainesville, FL (US); Garima Srivastava, Sunrise, FL (US)

(73) Assignee: AventuSoft, LLC, Sunrise, FL (US)

( * ) Notice: Subject to any disclaimer, the term of this patent is extended or adjusted under 35 U.S.C. 154(b) by 0 days.

(21) Appl. No.: 13/370,542

(22) Filed: Feb. 10, 2012

(65) Prior Publication Data

US 2012/0209132 A1  Aug. 16, 2012

Related U.S. Application Data

(60) Provisional application No. 61/463,069, filed on Feb. 11, 2011.

(51) Int. Cl.
  *A61B 7/00* (2006.01)
(52) U.S. Cl.
  USPC .......................................... 600/586
(58) Field of Classification Search
  USPC ............................ 600/528, 586; 381/67, 94.1
  See application file for complete search history.

(56) References Cited

U.S. PATENT DOCUMENTS

| | | |
|---|---|---|
| 6,005,951 A | 12/1999 | Grasfield et al. |
| 6,028,942 A | 2/2000 | Greenberger |
| 6,219,424 B1 | 4/2001 | Murphy |
| 6,295,365 B1 | 9/2001 | Ota |
| 6,368,283 B1 | 4/2002 | Xu et al. |
| 6,438,238 B1 | 8/2002 | Callahan |
| 6,650,940 B1 | 11/2003 | Zhu et al. |
| 6,661,161 B1 | 12/2003 | Lanzo et al. |
| 7,006,638 B1 | 2/2006 | Baekgaard et al. |
| 7,300,406 B2 | 11/2007 | Carter |
| 7,721,843 B1 | 5/2010 | Belenger et al. |
| 7,753,856 B2 | 7/2010 | Dziubinski |
| 7,819,814 B2 | 10/2010 | Gavriely et al. |
| 7,841,445 B2 | 11/2010 | Berk et al. |
| 7,909,772 B2 | 3/2011 | Popov et al. |
| 7,917,209 B2 | 3/2011 | Joo et al. |
| 7,940,937 B2 | 5/2011 | Smith |
| 7,991,165 B2 | 8/2011 | Kassal et al. |
| 2003/0208130 A1 | 11/2003 | Yotam et al. |
| 2006/0198533 A1* | 9/2006 | Wang et al. ............ 381/67 |

* cited by examiner

*Primary Examiner* — Brian T Gedeon
(74) *Attorney, Agent, or Firm* — Marc Boillot

(57) ABSTRACT

A system and method for visualizing auditory scene analysis by way of a portable device is provided. In one embodiment, the method steps include capturing multiple sounds from a sensor array of microphones connected to the portable device, performing auditory scene analysis on detected body sounds in accordance with a psychoacoustic representation of body organ functions, and rendering to a display of the portable device a visualization of auditory scene auscultation of the body sounds, including user input functionality for separated sound source tracks, sound source identifier tracks, and sound source location trajectories.

20 Claims, 8 Drawing Sheets

METHOD AND SYSTEM OF AN ACOUSTIC SCENE ANALYZER FOR BODY SOUNDS

CROSS REFERENCE TO RELATED APPLICATION

This application also claims priority benefit to Provisional Patent Application No. 61/463,069 filed on Feb. 11, 2011, the entire contents of which are hereby incorporated by reference.

FIELD OF THE INVENTION

The embodiments herein relate generally to clinical monitoring electronics and more particularly to sound analysis software and acoustic listening devices in medical practice.

BACKGROUND

Auditory scene analysis is the process by which the human auditory system organizes sound into perceptually meaningful elements. The three key aspects of the auditory scene analysis model are: segmentation, integration, and segregation. Auditory scene analysis addresses the problem of hearing in complex auditory environments. It uses a series of creative analogies to describe the process required of the human auditory system as it analyzes mixtures of sounds to recover descriptions of individual sounds.

In a clinical setting, the medical professional that listens to body sounds, for example, breathing sounds, bowel sounds, joint sounds, or heart beats, performs a type of mental auditory scene analysis. The clinician is trained to "listen" for certain types of expected sounds that can specifically lead to a proper diagnosis; those associated with the patients' health and well being. Through training, the clinician is taught to listen for certain disruptions or deviations of expected health body sounds. This act of listening (auscultation), directly or through a stethoscope or other instrument, to sounds within the body is a practical method of diagnosis.

Effectiveness of auscultation is however compromised in high environmental noise conditions, for example, in trauma centers, busy emergency rooms, and in the field, where various noises disrupt the listener's attention. It can be difficult for a clinician to discriminate and listen for subtle body sounds with competing sound sources, let alone, make a proper diagnosis. Also majority of the heart sound information is in the infrasound bandwidth below the human hearing threshold making it harder to diagnose a cardiovascular condition. Moreover, healthcare professionals with hearing impediment are limited in using auscultation as an effective technique for patient assessment.

Currently there are few useful models that can implement or realize auditory scene analysis. Fourier-type theory and computational auditory scene analysis techniques do not fully explain how the biological ear is able to "hear everything and listen to anything" even under very challenging environmental conditions—also known as the "cocktail party effect".

A need therefore exists for sound analysis systems that enhance listening utility and assist the clinician in their practice.

BRIEF DESCRIPTION OF THE DRAWINGS

The features of the system, which are believed to be novel, are set forth with particularity in the appended claims. The embodiments herein, can be understood by reference to the following description, taken in conjunction with the accompanying drawings, in the several figures of which like reference numerals identify like elements, and in which:

DETAILED DESCRIPTION

Figure 1A:
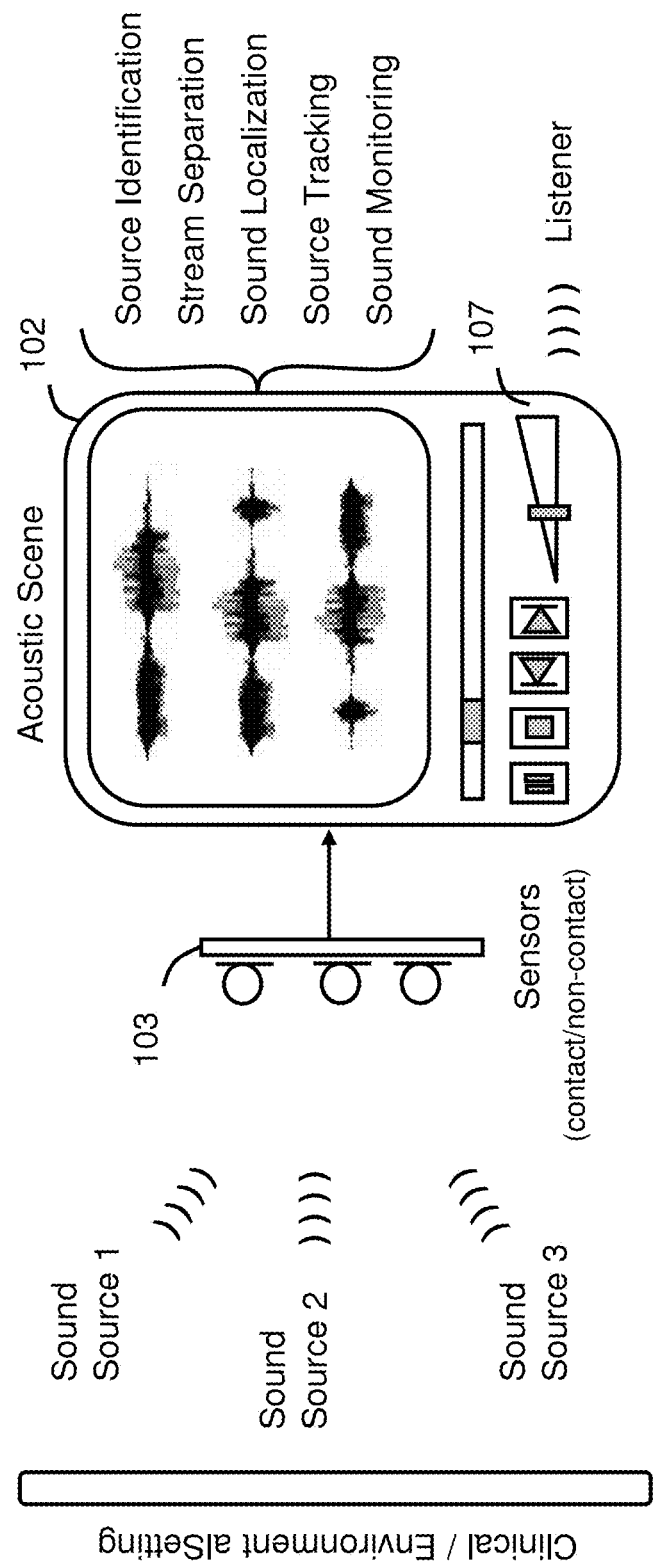
FIG. 1A illustrates a portable device for capturing and analyzing multiple sounds sources in a acoustic setting in accordance with one embodiment.

While the specification concludes with claims defining the features of the embodiments of the invention that are regarded as novel, it is believed that the method, system, and other embodiments will be better understood from a consideration of the following description in conjunction with the drawing figures, in which like reference numerals are carried forward.

As required, detailed embodiments of the present method and system are disclosed herein. However, it is to be understood that the disclosed embodiments are merely exemplary, which can be embodied in various forms. Therefore, specific structural and functional details disclosed herein are not to be interpreted as limiting, but merely as a basis for the claims and as a representative basis for teaching one skilled in the art to variously employ the embodiments of the present invention in virtually any appropriately detailed structure. Further, the terms and phrases used herein are not intended to be limiting but rather to provide an understandable description of the embodiment herein.

The exemplary embodiments and method of operation herein provide a biologically inspired system that models the physiological processes underlying the human auditory system's capacity for auditory scene analysis and provides visual display of sound separation, localization and tracking. It can be implemented in a single, low-power compact package that is easy-to-integrate, has low computational needs, a small microphone array footprint, to capture body sounds in real-world conditions. Specifically, psychoacoustic models are employed to separate audio signal captured through two or more sensors which can have a non-linear/non-uniform alignment. The embedded platform, the system, and implementation of psychoacoustic models, and related method are discussed in further detail below.

Referring to FIG. 1A, an illustration 100 of auditory scene analysis by way of the inventive device, and methods herein described, is shown. The portable device 102 provides visual auditory scene analysis of multiple sound sources within an environmental setting. The portable device 102 by way of the sensor 103 captures a composite signal of the multiple sound sources (S1, S2, S3, murmurs, etc) and then decomposes and reproduces each of the individual sound sources from this composite signal. It then visually displays location of the individual sound sources of the acoustic scene through the user interface 107 of the portable device 102. The user interface 107 in addition to providing visual separation of sound sources also permits playback of these individual sound sources as audio clips. Notably, each of these sound sources is an independent source of sound present in the environment, for example, spoken speech from clinicians talking in a clinical setting, from medical equipment creating audible sounds, or hospital announcements over an intercom.

The portable device 102, in addition to providing visual display of sound source separation of speech and acoustic sounds, also performs as a listening device for body sounds. In such arrangement, the device can be used in a clinical setting, for example, for performing auscultation. Briefly, auscultation is the process of listening to internal body sounds, and includes, for example, the technique of listening to chest sounds for the diagnosis of respiratory conditions, or heart sounds for the diagnosis of heart disorders using a stethoscope. Specialized clinicians perform accurate diagnosis using auscultation, but accurate diagnosis using the auscultation technique is problematic for pediatricians, internists, primary care physicians, physician assistants, registered nurses, nurse practitioners and other non-specialized healthcare professionals.

Figure 6:
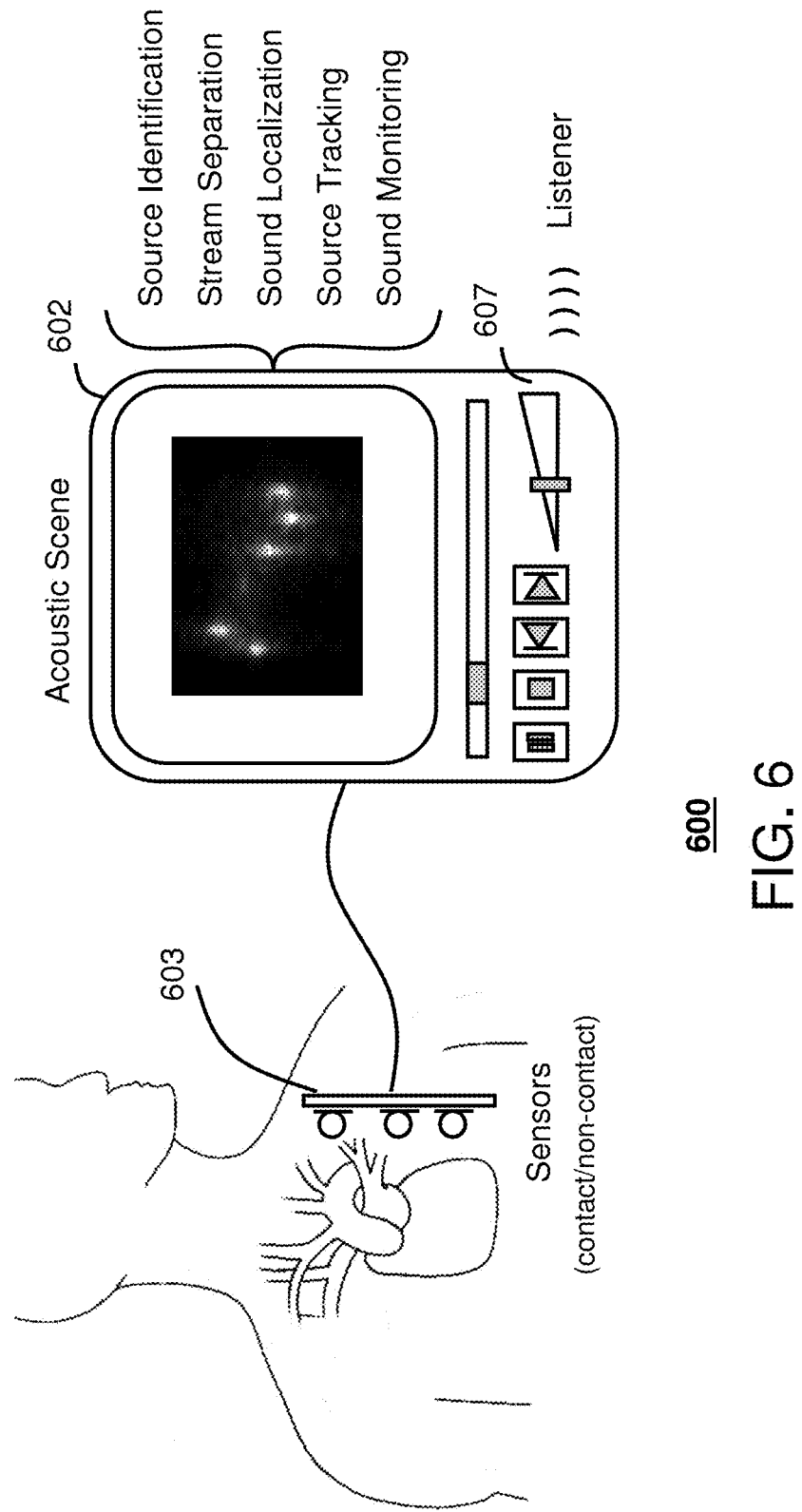
FIG. 6. illustrates an exemplary depiction of the portable device for capturing and analyzing heart sounds.

In such an arrangement, as shown in FIG. 6, the sensor array 603 is placed on the patient's chest to listen for heart sounds. The sensor array 603 is communicatively coupled to the portable device 602 to listen, process and analyze heart sounds. It should be noted that use of the portable device 602, does not require specialized training, is non-invasive, and allows non-cardiologists to provide adequate diagnostic capabilities for detecting normal and abnormal conditions of the cardiovascular system. In this embodiment, the exemplary portable device 602 and method of operation herein provide for visual auscultation will enable health care professionals to perform in-depth cardiovascular examinations that are more detailed than possible with current technology (auscultation of composite heart sounds) by providing a visual 2-dimensional representation of precise location of various heart sounds, arterial and ventricular septal defects, and systolic or diastolic murmurs and enables cardiovascular examinations without requiring hearing the heart sounds.

As one example, the portable device 102 can be deployed in a clinical setting to perform cardio-acoustic classification, screening, diagnosis and monitoring of cardiovascular condition, for instance, as disclosed in U.S. Provisional Patent Application No. 61/463,092 filed on Feb. 11, 2011, entitled "Method and System of a for Cardio-acoustic Classification system, for Screening, Diagnosis and Monitoring of Cardiovascular Conditions", the entire contents of which are hereby incorporated by reference. Other example for auscultation of respiratory sounds or other body sounds are herein contemplated.

Figure 1B:
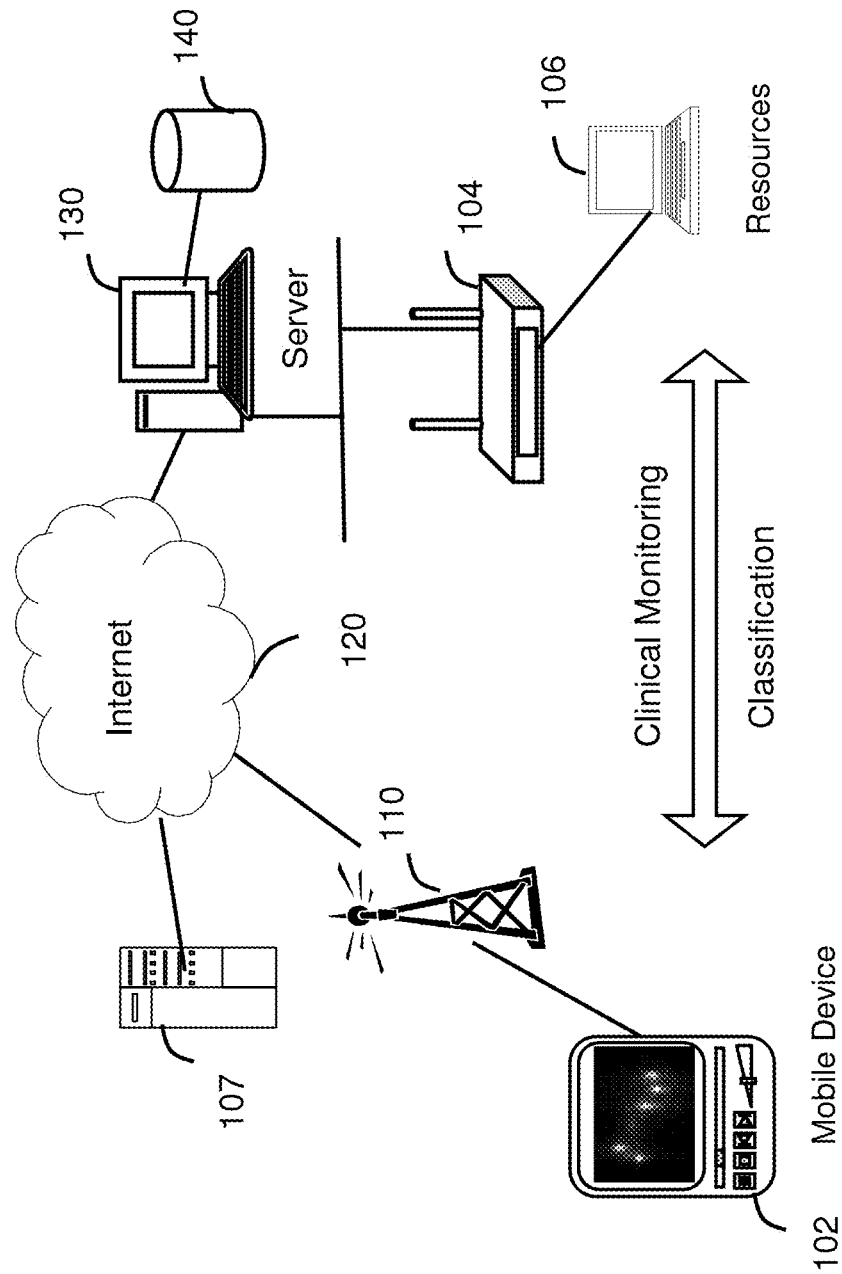
FIG. 1B illustrates a network for uploading the analysis and monitoring the multiple sound sources from the portable device of FIG. 1A in accordance in accordance with one embodiment.

Referring to FIG. 1B, a portable communication environment 190 is shown for visualization of auditory scene analysis by the portable device 102 and over a communication network. The environment 190 enables the portable device upon separating out acoustic sound sources, or body sounds, in accordance with the desired application, to upload and provide audio stream data and analyzed data over the network. Through this communication network and associated resources, the portable device can further classify sound sources, and monitor and report health-related or environmental indicators responsive to the classification of the sounds. As one example, it can transmit audio streams to a remote server for further specialized classification or request treatment options responsive to a body sound classification. As another example, it can detect and report failure of an audible medical device, or the presence of one or more persons in a room. As an auscultation device, it can assess and report normal and abnormal conditions of the cardiovascular system for both congenital and acquired heart diseases.

The portable communication environment 190 can provide wireless connectivity over a radio frequency (RF) communication network, a Wireless Local Area Network (WLAN) or other telecom, circuit switched, packet switched, message based or network communication system. In one arrangement, the portable device 102 can communicate with a base receiver 110 using a standard communication protocol such as CDMA, GSM, TDMA, etc. The base receiver 110, in turn, can connect the portable device 102 to the Internet 120 over a packet switched link. The internet can support application services and service layers 107 for providing media or content to the portable device 102. The portable device 102 can also connect to other communication devices through the Internet 120 using a wireless communication channel. The portable device 102 can establish connections with a server 130 on the network and with other portable devices for exchanging information. The server 130 can have access to a database 140 that is stored locally or remotely and which can contain profile data. The server can also host application services directly, or over the internet 120. In one arrangement, the server 130 can be an information server for entering and retrieving presence data.

The portable device 102 can also connect to the Internet over a WLAN 104. Wireless Local Access Networks (WLANs) provide wireless access to the portable communication environment 190 within a local geographical area. WLANs can also complement loading on a cellular system, so as to increase capacity. WLANs are typically composed of a cluster of Access Points (APs) 104 also known as base stations. The portable communication device 102 can communicate with other WLAN stations such as a laptop 103 within the base station area. In typical WLAN implementations, the physical layer uses a variety of technologies such as 802.11b or 802.11g WLAN technologies. The physical layer may use infrared, frequency hopping spread spectrum in the 2.4 GHz Band, or direct sequence spread spectrum in the 2.4 GHz Band. The portable device 102 can send and receive data to the server 130 or other remote servers on the portable communication environment 190. In one example, the portable device 102 can send and receive images from the database 140 through the server 130.

Figure 2:
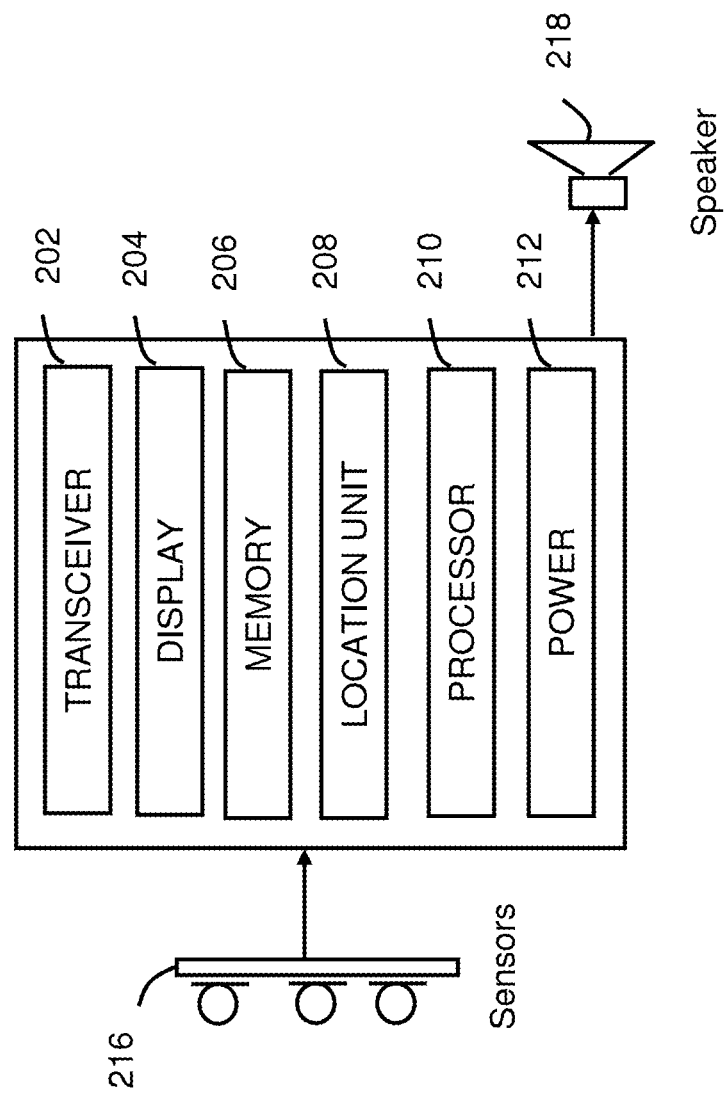
FIG. 2 depicts block diagram components of a portable device for visual rendering of auditory scene analysis in accordance with one embodiment.

FIG. 2 depicts an exemplary embodiment of the portable device 102 for providing visual display of auditory scene analysis for both air-transmitted acoustic sounds and internal body sounds. It comprises a wired and/or wireless transceiver 202, a user interface (UI) display 204, a memory 206, a location unit 208, and a processor 210 for managing operations thereof. The portable device 102 can be any smart processing platform with Digital signal processing capabilities, application processor, data storage, display, input modality like touch-screen or keypad, microphones, speaker, Bluetooth, and connection to the internet via WAN, Wi-Fi, Ethernet or USB. This embodies custom hardware devices, smartphone, cell phone, mobile device, iPad and iPod like devices, a laptop, a notebook, a tablet, or any other type of portable and mobile communication device. A power supply 212 provides energy for electronic components.

In one embodiment where the portable device 102 operates in a landline environment, the transceiver 202 can utilize common wire-line access technology to support POTS or VoIP services. In a wireless communications setting, the transceiver 202 can utilize common technologies to support singly or in combination any number of wireless access technologies including without limitation cordless phone technology (e.g., DECT), Bluetooth™ Wireless Fidelity (WiFi), Worldwide Interoperability for Microwave Access (WiMAX), Ultra Wide Band (UWB), software defined radio (SDR), and cellular access technologies such as CDMA-1X, W-CDMA/HSDPA, GSM/GPRS, TDMA/EDGE, and EVDO. SDR can be utilized for accessing a public or private communication spectrum according to any number of communication protocols that can be dynamically downloaded over-the-air to the communication device. It should be noted also that next generation wireless access technologies can be applied to the present disclosure.

The power supply 212 can utilize common power management technologies such as replaceable batteries, supply regulation technologies, and charging system technologies for supplying energy to the components of the communication device and to facilitate portable applications. In stationary applications, the power supply 212 can be modified so as to extract energy from a common wall outlet and thereby supply DC power to the components of the communication device 102.

The location unit 208 can utilize common technology such as a GPS (Global Positioning System) receiver that can intercept satellite signals and there from determine a location fix of the portable device 102.

The controller processor 210 can utilize computing technologies such as a microprocessor and/or digital signal processor (DSP) with associated storage memory such a Flash, ROM, RAM, SRAM, DRAM or other like technologies for controlling operations of the aforementioned components of the communication device.

The portable device 102 includes the sensors 216 for capturing normal sounds, noise sounds, voice signals, environmental sounds and body sounds. A speaker 218 is provided for playing audio or other sound media. One or more microphones are present in the sensor array for the computational auditory scene analysis based software and enhanced noise suppression, such as adaptive beam canceling, and one or more speakers 218 may be present for stereophonic sound reproduction. One or multiple microphones of the sensor array may be piezoelectric based to capture infrasound signals. These microphones consist of piezoelectric film sensor contacts to capture vibrations from infrasound and audible-sound regions with high fidelity. An additional benefit is that they do not capture environmental noise.

Figure 7:
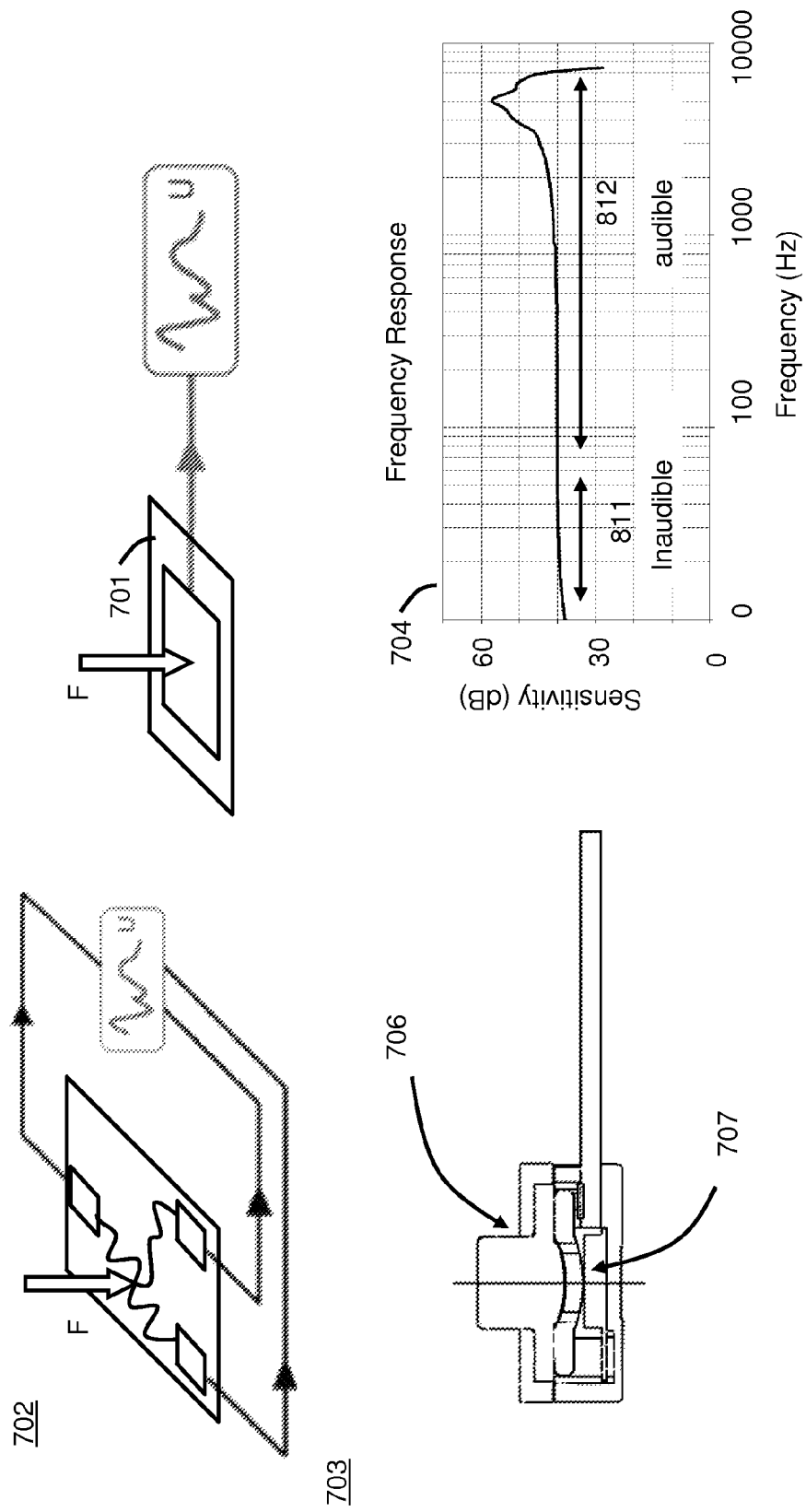
FIG. 7. illustrates the contact sensor's (microphones) to capture infrasonic and audible sounds.

Briefly referring ahead to FIG. 7, an exemplary embodiment 700 of a sensor array 702 for capturing infrasound and audible sound from the heart. The sensor array 702 includes multiple sensors 701 that pick up vibrations from the body and the air. In such combined form, the sensor array is capable of providing a frequency range 704 specific to sensitivity in the infrasound region 711 and also the audible region 712. In one arrangement as shown in 702, the sensors are placed in a non-collinear arrangement such that the position and magnitude of an applied force (F) can be localized; wherein the force is generated in response to a body function, for example, a joint sound responsive to an articulatory movement or muscle contraction. The processor evaluates the location of the force over time to generate a body signal vector; a mathematical quantity that has both magnitude and direction. In such arrangement, even though the force may be localized to a single spatial point (e.g., <x,y,z>) as shown in 702 on the surface of the sensor array, the physiological mechanisms which drive the point source that emanate from differing locations can be identified and tracked (e.g., bowel sounds, joint sounds, muscles etc.)

In one embodiment, as shown in 703, each sensor 701 includes a front sensing non-contact component 706 and a bottom sensing contact component 707. The contract component 707 can rest on the body surface to detect infrasound body sounds and vibration; direct contact provides a reduction in acoustic impedance to maximizes acoustic sound propagation of infrasound. Lower impedances permit for improved acoustic wave propagation. It comprises a flexible membrane that transforms shape responsive to mechanical forces, which is measured via the sensor. As one example, the membrane is a piezoelectric material that generates an electric voltage responsive to an applied force. The contact sensor also includes an adhesive, which can include a gel paste, to further enhance impedance matching. The non-contact component 706 embodies microphonic elements that are exposed to air to provide for capture of acoustic waveforms. It can react as a micro-electro mechanical microphone, elected or other type of condenser microphone responsive to acoustic waveforms. The sensor array 702 thus shares construct to embody contact sensors for body sounds on a back side and non-contact sensors on a front side for audible sounds, for example, the outer diaphragm support housing, certain electrical wiring traces, and integrated design layout.

In one arrangement, for auscultation, the sensors 216 capture heart sounds from the patient's heart by way of these microphones, which respond to both vibrations from infrasound, and 2) acoustically transmitted audible sound. Heart sounds are produced by the vibrations of the cardiohemic system, composed of the blood, heart walls and valves. The vibrations are triggered by the acceleration and deceleration of blood due to abrupt mechanical events of the cardiac cycle. Sounds present at the chest wall are the result of the heart muscles, together with the sound transmission characteristic of the heart and chest wall. A portion of sound produced by these vibrations lies in the human audible frequency range and a portion lies in the lower-frequency inaudible infrasound range. Heart sounds recorded on the chest wall are found between 0-1000 Hz with the main energy below 100 Hz.

Briefly, hearing sensitivity is explained through psychoacoustics, which is the study of sound perception and the relationship between sounds and its physiological and psychological effects. Hearing is not a purely mechanical phenomenon of air and fluid wave propagation, but is also a sensory and perceptual event; in other words, when a person hears something, that something arrives at the ear as a mechanical sound wave traveling through the air, but within the ear it is transformed into neural action potentials through fluid movement across the basilar membrane. Inner hair fibers on the basilar membrane are motioned back and forth responsive to the fluid movement. This mechanical movement generates action potentials due to the opening and closing of hair cell membranes which results in the passage of charged particles, thus generating electro-chemical gradients known as the action potentials. These nerve pulses then travel to the brain where they are perceived through higher level cognition processes. Hence, in many problems in acoustics, such as for audio processing, it is advantageous to take into account not just the mechanics of the environment, but also the fact that both the ear and the brain are involved in a person's listening experience.

Figure 3:
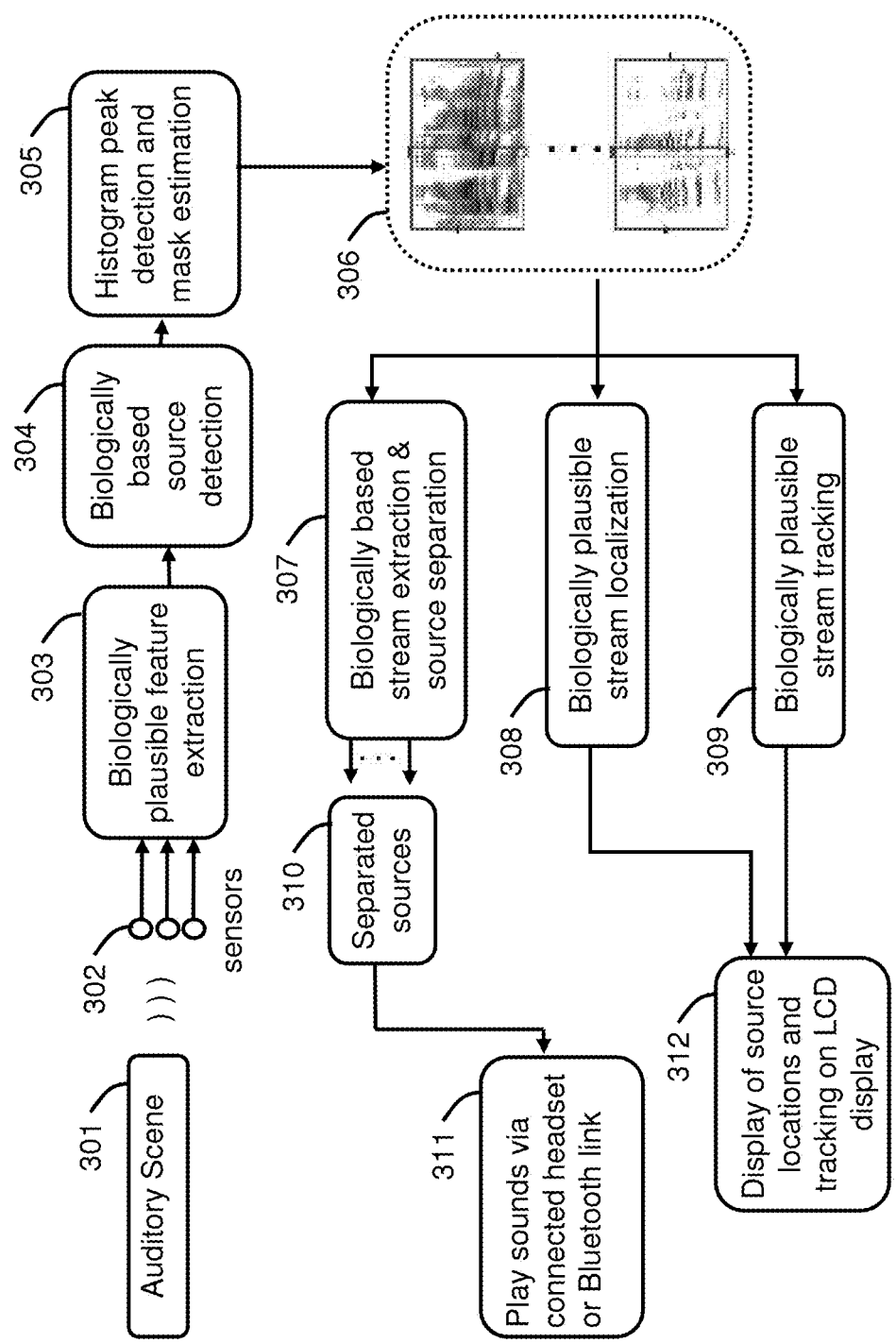
FIG. 3 illustrates an exemplary method for auditory scene analysis by way of the portable device in accordance with one embodiment.

The exemplary embodiments herein accordingly provide a device and method that incorporates both the mechanical aspect of hearing physiology and cognitive perception of sound for performing auditory scene analysis and visual rendering of sound streams. Referring now to FIG. 3, a method 300 for auditory scene analyzer of body sounds is herein provided. The method 300 can be provided with more or less than the number of steps shown. When describing the method 300, reference will be made to FIGS. 1-5, although it must be noted that the method 300 can be practiced in any other suitable system or device. The steps of the method 300 are not limited to the particular order in which they are presented in FIG. 3. The method can also have a greater number of steps or a fewer number of steps than those shown in FIG. 3.

The method 300 can start in state 301, for example, where the auditory scene 301 is a clinical setting, as illustrated in FIG. 1, where sensor array 103 of the portable device listens for internal body sounds. As one example, and for progressing through the description of method 300, the sensor array 103 of the portable device 102 is placed on the patient chest to listen for heart sounds. The sensor array at state 302, captures from the heart sounds, both vibrations from infrasound and acoustically transmitted audible sound, to serve as an enhanced stethoscope for performing auscultation wherein specific identified heart sounds are visually shown on the screen 312 and also audibly separated for individual classification and listening.

At step 303, biologically based feature extraction is performed on the body sounds. The portable device 102, by way of the processor 210 implementing a software module, extracts features from the auditory scene for analysis based on psychoacoustic properties of the input sound; for instance, those characteristics specific to body sounds and external sounds imparting detectable sound characteristics on the body sounds. In one arrangement, the processor 210 applies a psychoacoustically derived filter-bank to the captured sound signals to increase resolution below 100 Hz and enhance sensitivity to the lower frequency regions specific to the heart sounds. The filterbank is specific to the psychoacoustic characteristics of the infrasound and acoustically transmitted audible sounds. This can be done in conjunction with the feature extraction, prior to feature extraction, or as part of a noise suppression stage, depending on the desired programming implementation.

In one embodiment, the filter bank is derived from the extracted features. The feature extraction technique is inspired by an accurate model of the human auditory system, designed to match the human hearing performance in the 100-10,000 Hz region. Briefly, pressure changes in the air reach the ear drum and are transmitted to the cochlea. Pressure waves induce vibrations of the basilar membrane which in turn induce hearing strains of the inner hair cells. Frequency perception is derived from the position of the inner hair cells grouped in critical bands along the length of the cochlea. As one example, the processor 210 during frequency extraction encodes a time-frequency sound signal decomposition according to this frequency perception derived from inner hair cell activation responses grouped in critical bands along the basilar membrane.

At step 304, biologically based source detection is performed to identify unique sources from the composite signal of body sounds. As one example, the portable device 102 by way of the processor 210 implementing a software module calculates inter-aural time differences between body sounds captured at the multiple microphones for place-coding and localizing the sound source according to the inter-aural time differences. During this step, individual source streams are detected, for example, by marking acoustic segments associated with location cues and marking acoustic segments associated with know patterns. These marked locations will be examined in further stages of the auditory scene analysis ahead.

The portable device 102 by way of the processor 210 implementing a software module performs auditory scene analysis for source detection in accordance with a psychoacoustic interpretation of the captured body sounds. In one embodiment, the software module implements a coincidence detection model, a model derived from studies which suggests that the brain transforms information about the relative time of arrival of a sound and intensity of signal at the two ears into a 'place code'—a map of auditory space, allowing it to carryout successful localization. Neurons in the brain fire corresponding to a different interaural (between the ears) time difference (ITD) and interaural level difference (ILD). In addition the biological system depends on the spectral content of the stimulus to create the correct map of the auditory space. The software module implements both these biologically inspired approaches to localize multiple sound sources. This novel implementation results in a biologically based algorithm that is computationally efficient, requires a microphone array for accurate localization and performance At step 305, histogram peak detection and mask estimation is performed in preparation for source separation of individual streams, source localization, and source tracking. This step produces and marks psychoacoustic parameters from the extracted features pertinent to source identification and separation. In one configuration, it estimates the transfer function for individual streams for eventual source separation. It does this by emulating the sophisticated computational units and biological processes of the auditory cortex and cerebellum in the human brain. Notably, the emulation process realized in the software module is modeled on the neural architecture of the cerebellum, which is a richly connected network of neurons, each of which can respond differently to the same input. The outputs of neurons and synapses of the model, like those in the auditory cortex, depend in diverse ways on the recent history of their inputs to carry out real-time computations, like the brain during mental processes, on time-varying input streams that require integration of information over time.

In one arrangement, the processor 210, for enhancing mask estimate, non-linearly amplifies the heart sounds in the infrasound bandwidth below hearing threshold in accordance with a psychoacoustic compression to compensate for the biological representation of loudness, pitch and timbre of human hearing to produce the cardiac signal. This can encode masking effects in signal peaks analogous to the manner in which the cochlea masks frequency specific sounds across a human hearing scale. Progressive masking of high frequencies by lower frequencies occurs as amplitude rises, which the noise suppression emulates.

In another arrangement, the processor 210, for enhancing peak detection, non-linearly frequency shifts the sound signal in the infrasound bandwidth to the audible bandwidth in accordance with a human hearing frequency scale to compensate for the biological representation of loudness, pitch and timbre of human hearing to produce the cardiac signal. This can also encode masking effects in peaks of the histogram analogous to the manner in which the cochlea masks frequency specific sounds across a human hearing scale to permit audibility of the heart sound above human hearing sensitivity threshold.

The output of this step results in a histogram, analogous to a spectrogram, as shown 306. The histogram can be visually displayed to the portable device 102, as part of the auditory analysis and prior to visualization of the individual sound streams, shown in FIG. 1. The display can further display marked locations of interest, for example, to help the clinician visualize sound properties of cardiac structures and cardiac activities to be separated. These separate components of the heart sound are useful to diagnose particular heart dysfunctions by providing visual and auditory input to the physician.

Figure 4:
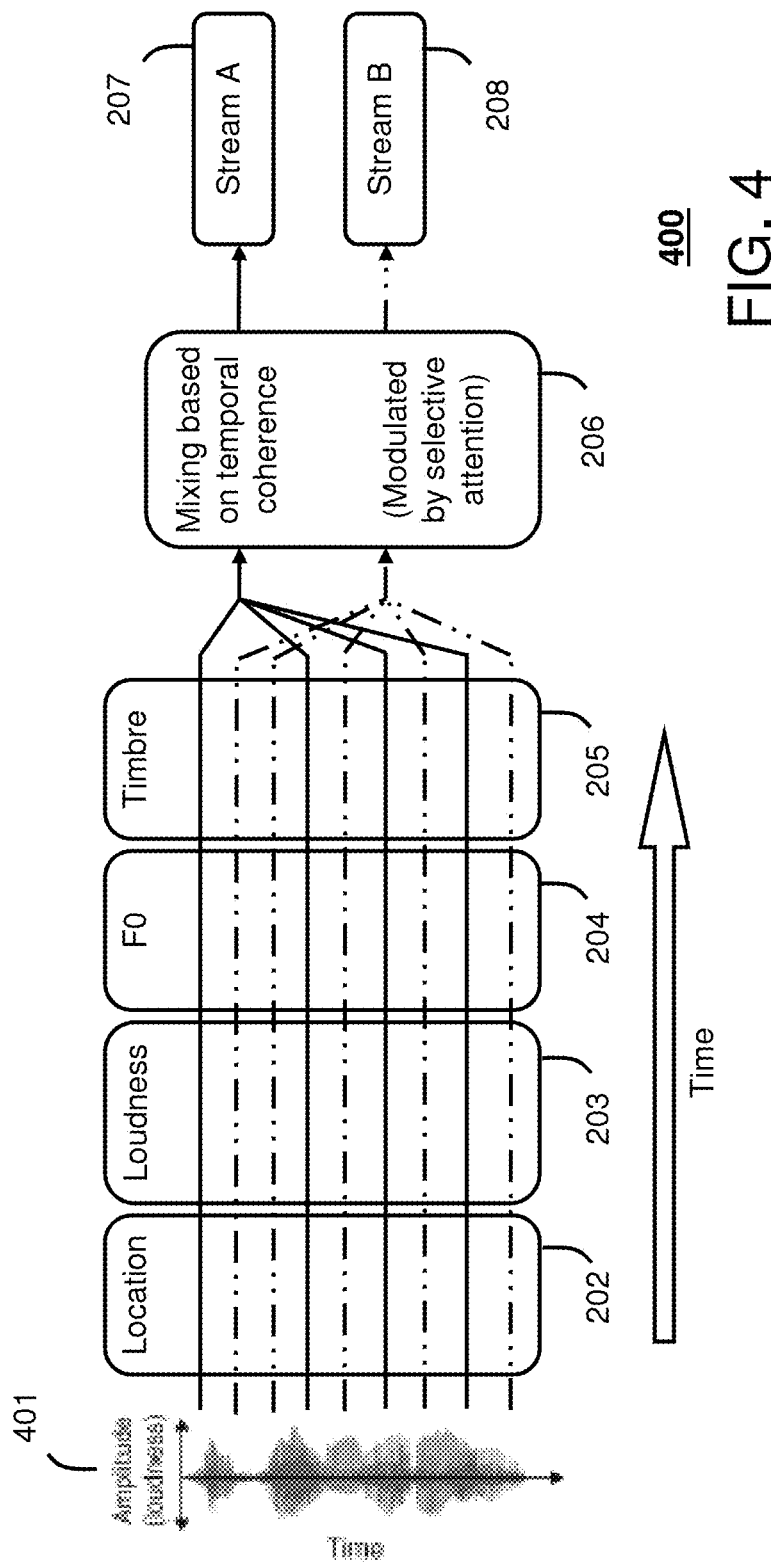
FIG. 4 illustrates an exemplary depiction of decomposing acoustic streams from a composite sound signal for visual display on the portable device in accordance with one embodiment.

At step 307, biologically based stream extraction and source separation is performed. During this step the portable device 102 identifies and separates individual streams. Referring briefly to FIG. 4, an exemplary depiction by way of this step for decomposing acoustic streams from a composite sound signal for visual display on the portable device in accordance with one embodiment will now be discussed. The composite signal 401 shown is a mixed sound signal, for example, comprising sound sources A and B. The biologically based stream extraction and source separation through the decomposition shown reproduces individual streams, as depicted by Stream A (207) and Stream B (208). The decomposition of the composite sound signal is represented by various tracks, each specific to a produced psychoacoustic parameter: location 202, loudness 203, fundamental frequency (f0) 204, and timbre (spectral envelope) 205.

Recall, the processor, by way of biologically based software modules, emulates the sophisticated computational units and processes of the auditory cortex and cerebellum in the human brain specific to auditory scene analysis. These time-varying connections and associated history are modeled as interconnected states and transitions in a state model. The states model spectral peaks, masked signals, acoustic cues, location cues, vibrations from infrasound and acoustically transmitted audible sound. For example, one state may be associated with the extracted features of infrasound specific to heart beak peaks, or heart murmurs below human auditory threshold. In another arrangement, the computational units model the opening and closing of a valve, while another state, or interconnected group of states, are associated with audible sounds, for instance, acoustic cues or patterns characteristic to regular and irregular heart functions associated with pre-learned mechanical events.

The software module implementing the state module above comprises two organizational processes: segmentation and grouping. Segmentation decomposes the auditory scene into time-frequency segments. Grouping combines the segments from the same source into a single perceptual stream. Within the grouping process, simultaneous organization integrates segments that overlap in time, and sequential organization groups segments across time.

On completion of biologically based stream extraction and source separation, the method 300 can continues to step 310, at which time the sources are separated for audible playback on the portable device 102 at step 311, or playback via a connected headset or Bluetooth link to other devices. Notably, the embedded platform of the portable device can be any smart processing platform with digital signal processing capabilities, application processor, data storage, display, input modality like touch-screen or keypad, microphones, speaker, Bluetooth, and connection to the internet via WAN, Wi-Fi, Ethernet or USB.

At step 308, biologically based stream localization is performed. During this step the portable device 102 assesses location specific information from the stream. As shown in FIG. 4, this includes the psychoacoustic parameters of location 202, loudness 203, fundamental frequency (f0) 204, and timbre (spectral envelope) 205. As one example, the localization of heart sounds, for example determining the origin of a valve opening or closing, is first determined by resolving detected acoustic cues associated with mechanical events (such as the acceleration/deceleration of blood flow), and then localizing the source of origin, for instance, triangulating the multiple acoustic signals captured at the multiple microphones. The processor 210 by way of the microphone array separated any number of sounds and provided sound localization, allows the clinician to easily identify where the sounds are originating. As previously noted, the software module implements a coincidence detection model for triangulation that provides a 'place code'—a map of auditory space, allowing it to carryout successful localization.

At step 309, biologically based stream tracking is performed on the body sounds in accordance with the produced psychoacoustic parameters. During this step the portable device 102 tracks individual streams based on the determined psychoacoustic parameters and the two determined organizational processes: segmentation and grouping. Tracking is achieved by through the two modalities (location and features extracted from signal), for stream clustering, on the premise that: 1) location cues permit excellent short-term discrimination between sources, but provide no stream identity information (i.e. a source can move while silent and then begin again elsewhere), and 2) acoustic cues (feature extraction) carry long-term source identity information, but a minimum duration is needed to build reliable source models.

The processor through auditory scene analysis tracks individual sound sources over time and space. It implements both short-term and long-term discrimination between sources, where short-term pertains to tracking individual stream when they are captured simultaneously as part of the composite signal, and long-term tracking pertains to tracking individual streams when they are absent for a certain duration of time and re-appear, or in other words, tracking sources as they transition in and out of auditory scene.

Figure 5:
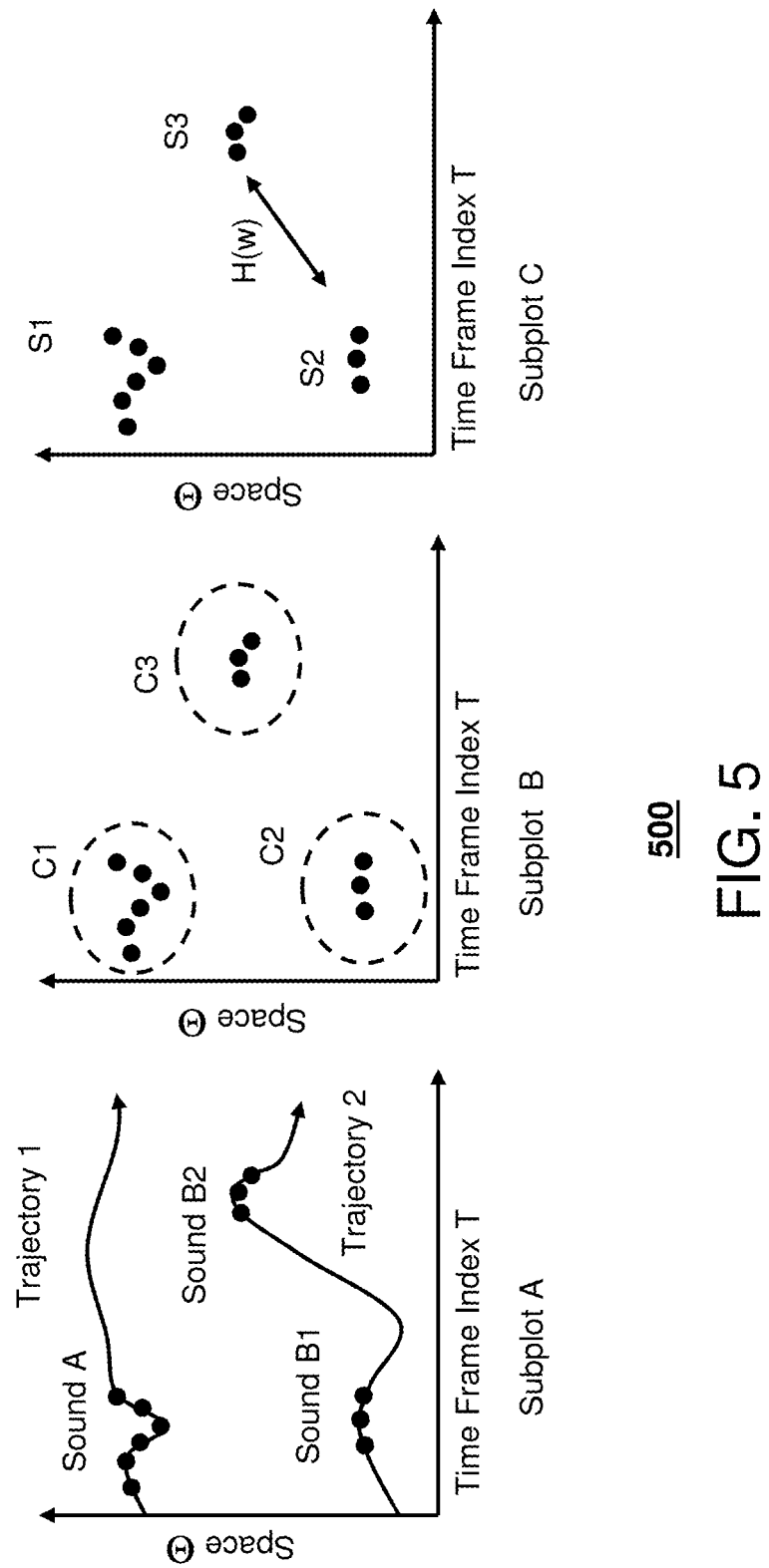
FIG. 5 illustrates an exemplary depiction of tracking and segmentation of a composite sound signal into independent streams in accordance with one embodiment.

Referring briefly to FIG. 5, an exemplary depiction of tracking and segmentation of a composite sound signal into independent streams in accordance with one embodiment. As shown, the methodology for stream tracking based on grouping and segmentation first identifies sound characteristics associated with an isolated sound source, which is performed in method 300 steps 303 to 305. As shown in subplot A, this first step produces a trajectory for each sound source. Once the sound source trajectories are created, the next step in the sequence of the methodology, short-term clustering of the sounds signals based on source identify is performed. The clusters are mapped in a feature space$\Theta$ with respect to time. The third step of the sequence shows the identification of the speech clusters into specific sources, allowing for tracking of sources through regions of silence while the source is moving around. The spatial interconnection is modeled by a transfer function H(w) for tracking the sound source through periods of silence.

Returning back to method 300 of FIG. 3, upon completing the biologically inspired stream localization and stream tracking, the source locations and tracks can be presented and rendered to the portable device 102, or any other communicatively coupled visualization platform, as shown in step 312. In one embodiment, this method of acoustic separation and localization of cardiovascular sounds provides separation and localization of heart sounds. Through analysis and detection of mechanical events, such as the opening and closing of valves, it is also able to isolate and localize heart murmurs allowing a physician to easily identify where the sounds are originating.

FIG. 6 shows one such embodiment for displaying heart sounds. 603 are the sensors placed over the chest. 602 shows the source identification, localization of the various heart sounds. This visual representation of the separate components of the heart sound are useful to diagnose particular heart dysfunctions by providing visual and auditory input to the physician. The source tracking and source monitoring provides information of the amount and direction of blood flow at each source location, which can be color coded on the display 204. The source separation allows the functionality to listen to any of the sources using 607. The embodiments of the invention as illustrated and described in FIG. 6 can be used for diagnosis of medical conditions from other body sounds such as lung sounds, bowel sounds, sounds from joints, etc, It will be apparent to those skilled in the art that various modifications may be made in the present invention, without departing from the spirit or scope of the invention. Thus, it is intended that the present invention cover the modifications and variations of this invention provided they come within the scope of the method and system described and their equivalents.

For example, variations of the exemplary embodiments describe a portable solution that can be used in the prevention and treatment of heart failure, prenatal and postnatal detection of congenital heart defects, military and athletic screening assessment and monitoring of cardiovascular status. This information can be reported locally to the immediate user, or by way of the network 120 and location unit 308, the portable device can report a user's location for scenarios requiring critical attention.

In another embodiment of the system and method, sounds produced by other cardiac structures and cardiac activities can also be separated. These separate components of the heart sound are useful to diagnose particular heart dysfunctions by providing visual and auditory input to the physician as well as to further diagnostic algorithms.

In another embodiment, the system and method described herein make it possible to analyze abnormalities occurring in specific source sites by processing the body sound. By separating the composite sound into sound components due to individual body structures and body activities, the algorithm can find the actual number and kinds of sources, the role they play in producing the sound, and concurrently pinpoint the location of an abnormality.

The exemplary embodiment of system and method herein also describe the development on an embedded hardware system, the main elements required to capture body sounds are the sensor unit that captures the body sounds, digitization, and digital processing of the body sounds for noise reduction, filtering and amplification. The diagnostic technique provided on the embedded platform broadly includes but is not limited to providing auditory scene analysis capabilities of mimicking the human ability to hear sounds inside a human body by separating multiple audio streams from composite sound, localizing the sounds precisely in real-time while using few microphones and providing a novel way to display the acoustic scene to the user.

Where applicable, the present embodiments of the invention can be realized in hardware, software or a combination of hardware and software. Any kind of computer system or other apparatus adapted for carrying out the methods described herein are suitable. A typical combination of hardware and software can be a portable communications device with a computer program that, when being loaded and executed, can control the portable communications device such that it carries out the methods described herein. Portions of the present method and system may also be embedded in a computer program product, which comprises all the features enabling the implementation of the methods described herein and which when loaded in a computer system, is able to carry out these methods.

While the preferred embodiments of the invention have been illustrated and described, it will be clear that the embodiments of the invention is not so limited. Numerous modifications, changes, variations, substitutions and equivalents will occur to those skilled in the art without departing from the spirit and scope of the present embodiments of the invention as defined by the appended claims.

What is claimed is:

1. A portable device for visualizing auditory scene auscultation of body sounds, the portable device comprising:
A visual display with user input; a sensor array of microphones to capture body sounds;
a processor coupled to the visual display and the sensor array configured to:
perform auditory scene analysis in accordance with a psychoacoustic interpretation of the captured body sounds;
render to the display a visualization of auditory scene auscultation of the body sounds, including:
separated sound source tracks; sound source identifier tracks; and sound source location trajectories,
a speaker coupled to the processor to play the separated sound source tracks responsive to user input; and
a power supply to provide power to electronic components of the portable device.

2. The portable device of claim 1, wherein the sensor array captures from body sounds both vibrations from infrasound and acoustically transmitted audible sound.

3. The portable device of claim 1, where the processor programmed in coupled sequence:
a first software module to extract features from the auditory scene analysis based on psychoacoustic characteristics of the body sounds;
a second software module to identify unique sources of the body sounds from the features; and a third software module to estimate masking patterns of each identified sound source based on sound generation characteristics of the sound sources.

4. The portable device of claim 3, further comprising:
a memory that stores frequency masking characteristics of multiple body organs,
wherein the processor evaluates the frequency masking characteristics of the multiple body organs for separating identified sound sources.

5. The portable device of claim 4, where the memory stores masking patterns of regular and irregular: heartbeat conditions, respiratory conditions, and gastrointestinal conditions.

6. The portable device of claim 2, further comprising in coupled sequence:
a fourth software module to perform sound source separation based on the identified unique sound sources, masking patterns, and extracted features.

7. The portable device of claim 2, further comprising in coupled sequence:
a fifth software module to localize sound sources and generate a location for identified sound sources; and
a sixth software module to track the location of the identified sound sources.

8. A method for visualizing auditory scene auscultation of body sounds by way of a portable device, the method comprising the steps of:
capturing body sounds from a sensor array detecting both vibrations from infrasound and acoustically transmitted audible sound connected to the portable device;
performing auditory scene analysis on the captured body sounds in accordance with a psychoacoustic representation of body organ functions;

rendering to a display of the portable device a visualization of auditory scene auscultation of the body sounds, including: separated sound source tracks, sound source identifier tracks; and sound source location trajectories.

9. The method of claim 8, comprising sound source tracking by:
   short-term monitoring of location cues to discriminate distances between sources; and
   long-term monitoring of acoustic cues for resolving features associated with sound source identities,
   wherein the location cues and acoustic cues are selectively stored and retrieved in a history within a memory of the portable device according to a coincidence detection model.

10. The method of claim 8, comprising calculating inter-aural time differences between body sounds captured at the microphone for place-coding and localizing the sound source according to the inter-aural time and level differences.

11. The method of claim 8, comprising calculating a biological representation of loudness, frequency, timbre and pitch for analyzing abnormalities occurring in identified sound source sites.

12. The method of claim 8, comprising separating a composite signal of the body sounds into sound components dues to individual body structures and body activities.

13. The method of claim 8, analyzing abnormalities occurring in specific source sites and reporting a location of the abnormality.

14. The method of claim 8, performing amplitude compression and frequency compression of the captured body sound in accordance with the psychoacoustic mapping procedure to compensate for the biological representation of loudness, pitch and timbre of human hearing.

15. The method of claim 8, comprising translating inaudible acoustic signals in a masked frequency region of an identified body organ sound spectrum to frequencies in an audible frequency region according to a psychoacoustic frequency mapping.

16. The method of claim 8, comprising generating a two-dimensional representation of locations of various heart sounds, arterial and ventricular septal defects, and systolic or diastolic murmurs.

17. A portable device for visualizing auscultation of body sounds, the portable device comprising:
   a visual display with user input;
   a sensor array of microphones to capture body sounds comprising vibrations from infrasound and acoustically transmitted audible sound;
   a processor coupled to the visual display and the sensor array programmed with sequential order of processing:
   a first software module to extract features from an auditory scene analysis based on psychoacoustic characteristics of the body sounds;
   a second software module to identify unique sources of the body sounds from the features;
   a third software module to estimate masking patterns of each identified sound source based on sound generation characteristics of the sound sources;
   a fourth software module to perform sound source separation based on the identified unique sound sources, masking patterns, and extracted features;
   a fifth software module to localize sound sources and generate a location for identified sound sources; and
   a sixth software module to track the location of the identified sound sources,
   wherein the processor determines if the sensor array is in non-body contact or body contact and compensates accordingly during psychoacoustic interpretation of the captured body sounds, and renders to the display a visualization of auditory scene auscultation of the body sounds.

18. The portable device of claim 17, further comprising a speaker or headset coupled to the processor to play the separated sound source tracks responsive to user input.

19. The portable device of claim 17, wherein the processor includes a
   software module for two organizational processes:
   segmentation to decompose the auditory scene into time-frequency segments; and
   grouping to combine the time-frequency segments from a same source into a single perceptual stream.

20. The portable device of claim 19, wherein with the grouping:
   simultaneous organization integrates time-frequency segments that overlap in time, and
   sequential organization groups segments across time.

* * * * *